US00PP11781P2

(12) United States Plant Patent
Krans et al.

(10) Patent No.: US PP11,781 P2
(45) Date of Patent: Feb. 20, 2001

(54) BERMUDAGRASS PLANT NAMED 'MS-SUPREME'

(75) Inventors: Jeffrey V. Krans, Starkville; Herbert W. Philley, Mathiston, both of MS (US)

(73) Assignee: Mississippi State University, Mississippi State, MS (US)

( * ) Notice: Under 35 U.S.C. 154(b), the term of this patent shall be extended for 0 days.

(21) Appl. No.: 09/055,230

(22) Filed: Apr. 6, 1998

(51) Int. Cl.[7] ..... A01H 5/00
(52) U.S. Cl. ..... Plt./389
(58) Field of Search ..... Plt./389

(56) References Cited

U.S. PATENT DOCUMENTS

| | | | | |
|---|---|---|---|---|
| P.P. 9,888 | * | 5/1997 | Brown et al. | Plt./398 |
| P.P. 10,289 | | 3/1998 | Krans et al. | Plt./389 |
| P.P. 10,290 | | 3/1998 | Krans et al. | Plt./389 |
| P.P. 10,332 | | 4/1998 | Krans et al. | Plt./389 |
| P.P. 11,163 | * | 12/1999 | Hanna | Plt./389 |

OTHER PUBLICATIONS http://www.ntep.org/prelim_report/onsite/prelimos99.htm, May 2000.*
http://www.ntep.org/onsite/ostbt98–99–4.htm, May 2000.*
Harlan, Jack R., J. M. J. de Wet, Wayne W. Huffline & John R. Deakin, Bulletin B–673 "A Guide to the Species of CYNODON (Graminaceae)" pp. 5–37 Oklahoma State University Agricultural Experiment Station, Jan. 1970.*

Krans, J. V., Philley, H. W., Gaotely, J. M. and Maddox, V. L. "Registration of MS–Supreme Bermudagrass", Crop Science vol. 39 No. 1, pp. 287, Jan. 1999.*

* cited by examiner

*Primary Examiner*—Howard J. Locker
*Assistant Examiner*—Wendy A Baker
(74) *Attorney, Agent, or Firm*—Piper, Marbury, Rudnick & Wolfe, LLP; Steven B. Kelber

(57) ABSTRACT

The subject of the present disclosure is a new and distinct variety of bermudagrass, designated experiment number MSB40 and named 'MS-Supreme' and is characterized by its natural dark green color (7.5 GY 5/6, Munsell© Color Charts) and enhanced dark green color (7.5 GY 4/6, Munsell© Color Charts) during overcast weather and the fall season, ultra-dwarf leaf blade length (6 mm) and width (0.5 mm), highly prostrate growth habit, and affords excellent turfgrass putting green quality under putting green culture.

6 Drawing Sheets

BACKGROUND OF THE INVENTION

1. Field of the Invention

The present invention relates to a new and distinct variety of bermudagrass, the variety being principally characterized by a darker green summer color, enhanced fall season and overcast weather color and higher shoot density than known bermudagrass.

2. Description of the New Variety

The variety is a new and distinct cultivar taxonomically identified as *Cynodon×magennisii* that was discovered growing under cultivation as a small inclusion in a 'Tifgreen' (unpatented) bermudagrass (*Cynodon dactylon×C. transvaalenis*) putting green (No. 14) at the Gulf Shores Country Club, Gulf Shores, Ala. (located approx. latitude 30'15.00 N and longitude 87°39.00 W). This new and distinct cultivar was noticed as an inclusion during extended periods of wet, overcast weather by expressing a darker green color and higher shoot density compared to the surrounding grass. A 5 cm diameter sample plug was taken from the center of the new and distinct cultivar and designated as 'MS-Supreme'. The sample plug was transplanted to a fumigated 1 $m^2$ field plot along with 23 other ecotypes previously collected and located at the Mississippi Agricultural and Forestry Experiment Station Plant Science Research Farm, Starkville, Miss. The 'MS-Supreme' and other plots were mowed, fertilized, and watered to promote growth such that all plots had a uniform and dense turf cover by the fall of 1991. During the time period from 1992 to 1996, the 1 $m^2$ plot of 'MS-Supreme' revealed a dark green summer season color (7.5 GY 5/6, Munsell© Color Charts) and enhanced dark green fall season color (7.5 GY 4/6, Munsell© Color Charts), high shoot density, short leaf length (4 to 8 mm) and narrow leaf width (0.4 to 1.0 mm), and extremely prostrate growth habit. 'MS-Supreme' has been vegetatively re-propagated using plugs (5 to 10 cm diameter) and sprigs (stolon segments of 3 to 10 cm long) taken from the initial 1 $m^2$ field plot at the Mississippi Agricultural and Forestry Experiment Station Plant Science Research Farm in Starkville, Miss. or from a secondary 5 $m^2$ plot at the Mississippi Agricultural and Forestry Experiment Station Plant Science Research Farm initiated in 1996 through sprigging. Other experimental plantings of 'MS-Supreme' using plugs have been made at the Mississippi State University Golf Course practice green in Starkville, Miss. (Jun. 1995), the Houston Country Club practice green in Houson, Tex. (May 1996) and Sturgis Sod Farm in Sturgis, Miss. (May 1998). Other experimental plantings of 'MS-Supreme' using sprigs have been made at the Tupelo Country Club practice green in Tupelo, Miss. (Jun. 1995), the Burning Tree Country Club practice green in Decatur, Ala. (Jun. 1995), the Deerfield Country Club experimental green in Madison, Miss. (May 1998) and the National Turfgrass Evaluation Program (NTEP) On-Site Bermudagrass test locations (May-July 1998). All experimental plantings of 'MS-Supreme' using plugs or sprigs have retained their true-to-type morphology. In 1996, a greenhouse study was conducted that measured the comparative plant morphology of 'MS-Supreme', 'Tifgreen', the putting green cultivar 'MS-Supreme' emerged from in Gulf Shores and 'Tifdwarf' (unpatented) bermudagrass (*C. dactylon*×*C. transvaalensis*), the closest known Cynodon cultivar. 'MS-Supreme', 'Tifgreen', and 'Tifdwarf' were each planted in six 15-cm diameter pots using representative stolon segments of each genotype and grown under optimum greenhouse conditions. All grasses were clipped daily until they fully covered the pots, then grown unclipped for three weeks and sampled. One stolon segment was randomly sampled from each pot and measured to determine their comparative morphology using the newest visible node, the leaf blade and sheath attached to that node, and the internode found preceding that node. After the initial sampling, pots were again regrown and sampled a second and third time according to the above procedures. All genotypes were sampled a total of three times yielding 18 observations per genotype. 'MS-Supreme' leaf blade length was significantly (P=0.05) shorter (10.1 mm) and the width narrower (1.5 mm) than 'Tifgreen' (length=39.1 mm and width=1.9 mm( and 'Tifdwarf' (length=24.9 mm and width=1.7 mm). The internode length of 'MS-Supreme' was significantly shorter (length=10.6 mm) and diameter smaller (0.5 mm) than 'Tifgreen' (length=19.9 and diameter=0.7 mm). There was no difference in internode length or diameter between 'MS-Supreme' and 'Tifdwarf'. Evaluations of the turfgrass quality of experimental putting green plots of 'MS-Supreme', 'Tifgreen', and/or 'Tifdwarf' were made at the Mississippi State Univerisity Golf Course, Starkville, Miss.; Tupelo Country Club, Tupelo, Miss.; and Burning Tree Country Club, Decatur, Ala. from 1995 to 1997. All plots were evaluated on a visual rating scale of turfgrass putting green quality of 1 to 9; with 1=poor quality, and 9=excellent quality. At the Mississippi State University Golf Course location, 'MS-Supreme' had the highest quality ratings (QR's) at the two mowing heights tested (7.8 QR at 3 and 5 mm mowing heights) compared to 'Tifdwarf' (6.1 QR at 3 mm and 6.9 QR at 5 mm) and 'Tifgreen' (4.9 QR at 3 mm and 5.3 QR at 5 mm). Evaluations at Tupelo Country Club revealed higher quality ratings for 'MS-Supreme' (7.8 QR) compared to 'Tifdwarf' (6.5 QR). At Burning Tree Country Club, quality ratings for 'MS-Supreme' were highest (7.7 QR) compared to 'Tifgreen' (4.5 QR) and 'Tifdwarf' (7.0 QR). The higher quality 'MS-Supreme' compared to the other grasses is attributed to its dark green summer color and enhanced dark green fall color, ultra-dwarf leaf morphology, and extremely prostrate growth habit. 'MS-Supreme', the new and distinct Cynodon cultivar and 'Tifdwarf', the closest known Cynodon cultivar were characterized using DNA amplification fingerprinting (DAF) analysis using primer 8.6i. The DAF analysis of 'Tifdwarf' showed the presence of a DNA band at 370 bps and absence of a bands at 200 bps, whereas; the same analysis of 'MS-Supreme' revealed the absence of a DNA band at 370 bps and the presence of a band at 200 bps. This analysis is evidence that the cultivars are different and can be positively identified without relying solely on morphological and performance traits. During out 6+ years of greenhouse and field observations of 'MS-Supreme', seedhead formation has not been observed. Under these same conditions, 'Tifgreen' and 'Tifdwarf' formed noticeable seedheads. Our evaluation of 'MS-Supreme' following repeated asexual greenhouse and field propagation has revealed that this new and distinct cultivar remained stable and distinct in its morphological features and turf performance characteristics.

The most noticeable variations among 'MS-Supreme', 'Tifgreen', and 'Tifdwarf' are that the new and distinct claimed cultivar 'MS-Supreme', has a dark green summer color (7.5 GY 5/6, Munsell© Color Charts) and enhanced fall season and overcast weather color (7.5 GY 4/6, Munsell©Color Charts) an ultra-dwarf leaf blade length (10.1 mm) and width (1.5 mm), and extremely prostrate growth habit. These features contribute to the high turfgrass putting green quality ratings measured at the 3 experimental putting green test sites. 'Tifdwarf', the closest Cynodon cultivar 'MS-Supreme' is well distinguished from 'MS-Supreme' in the fall season by its anthocyanin color (purple leaf and stolon cast), which is not present in 'MS-Supreme', and by different DNA amplification profiles using DAF analysis. 'Tifgreen', the genotype from which 'MS-Supreme' emerged is well distinguished from 'MS-Supreme' by its erect growth habit and large sized leaves and stolons. 'MS-Supreme', the new and distinct claimed cultivar is illustrated in the accompanying photographs in comparison with 'Tifgreen' and 'Tifdwarf' bermudagrass.

BRIEF DESCRIPTION OF THE DRAWINGS

FIG. 1 is a photograph of the comparative morphology of stolon segments taken from plants grown in pots and managed unclipped for 3 weeks. The stolon on the left in the photograph is the new and distinct Cynodon cultivar 'MS-Supreme', the middle stolon segment in the photograph is the closest known Cynodon cultivar 'Tifdwarf', and the stolon segment on the right in the photograph is the Cynodon cultivar from which 'MS-Supreme' emerged, 'Tifgreen'. This photograph shows the shorter leaf blade leaf (10.1 mm) and width (1.5 mm) of 'MS-Supreme' compared to 'Tifdwarf' and 'Tifgreen'.

FIG. 2 is a photograph illustrating the comparative morphology of whole plants grown in pots and managed unclipped for 3 weeks. The pot on the left in the photograph is the new and distinct Cynodon cultivar, 'MS-Supreme'. The center pot in the photograph is the closest known Cynodon cultivar, 'Tifdwarf'. The pot on the right in the photograph is the Cynodon cultivar from which 'MS-Supreme' emerged, 'Tifgreen'. This photograph shows the more dwarf stature of 'MS-Supreme' compared to 'Tifdwarf' and 'Tifgreen'.

FIG. 3 is a photograph of unclipped greenhouse grown trays of the new and distinct Cynodon cultivar 'MS-Supreme', illustrating its extremely prostrate growth habit.

FIG. 4 is a photograph of the field plots of Cynodon cultivars grown at the Mississippi State University Golf Course experimental putting green site. The field plot in the lower left corner is 'Tifgreen', and is the Cynodon cultivar from which 'MS-Supreme' emerged, the field plot in the lower right corner is 'MS-Supreme', the new and distinct Cynodon cultivar, and the field plot in the upper left mid-level position is 'Tifdwarf', the closest known Cynodon cultivar. This photograph illustrates the higher turfgrass quality of 'MS-Supreme' compared to the Cynodon cultivars 'Tifdwarf' and 'Tifgreen' when grown under putting green culture.

FIG. 5 is a photograph of sod pieces taken from field plots of Cynodon cultivars grown at the Mississippi State University Golf Course experimental putting green site. The bottom sod piece is 'MS-Supreme', the new and distinct Cynodon cultivar, and the top sod piece is 'Tifdwarf', the closest known Cynodon cultivar. This photograph illustrates the shorter and more narrow leaves and higher shoot density of 'MS Supreme' compared to 'Tifdwarf' when grown under putting green culture.

DETAILED DESCRIPTION OF THE NEW PLANT

Figure 6:
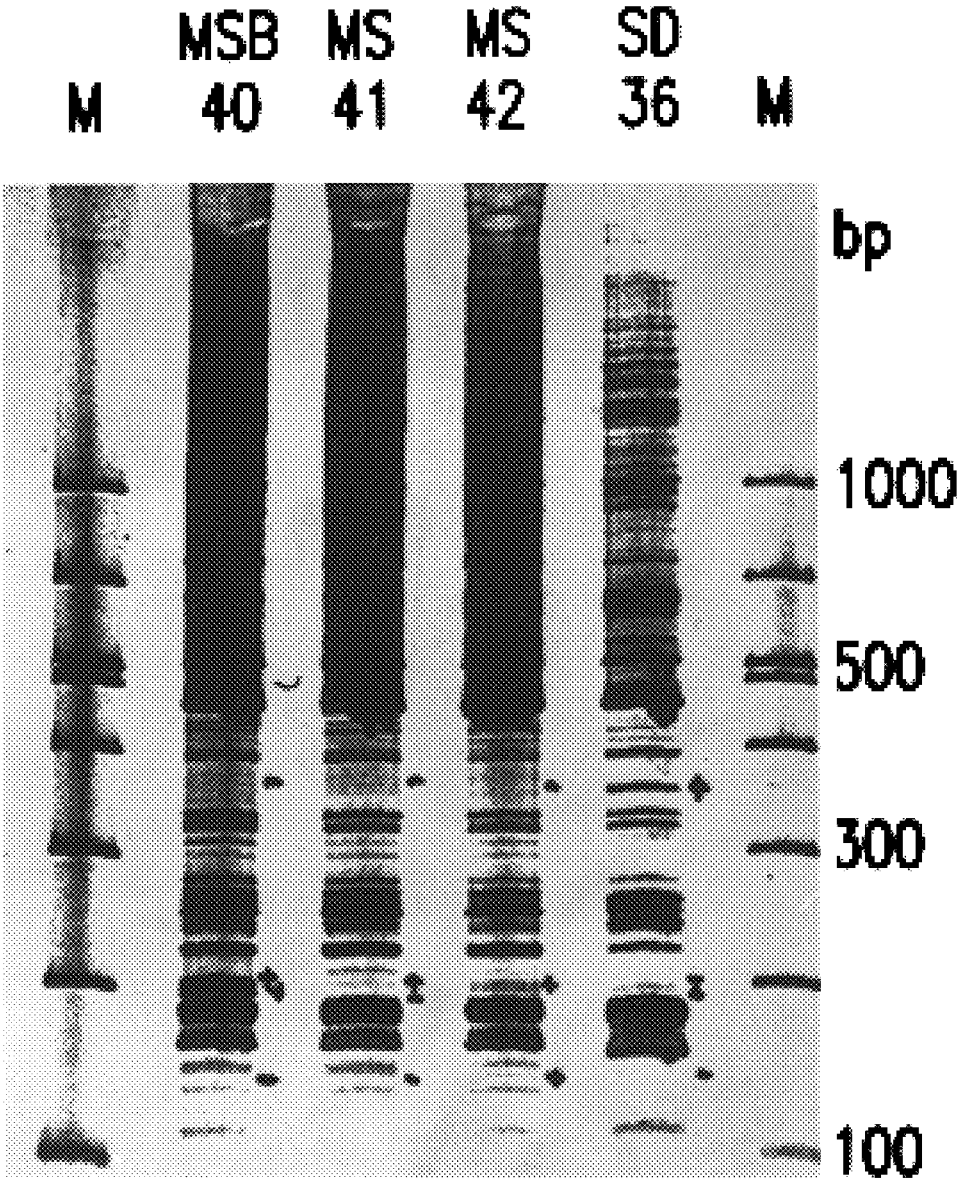
FIG. 6 is a photograph of DNA amplification profiles (generated with DAF and primer 8.6i) of Cynodon cultivars. The second profile from the left is 'MS-Supreme' (labeled MSB40), the new and distinct Cynodon cultivar, and the profile on the far right is 'Tifdwarf' labeled SD36), the closest known Cynodon cultivar. This photograph illustrates that 'MS-Supreme' is different from 'Tifdwarf' by the presence of a band at 200 bps and the presence of a band at 370 bps in 'MS-Supreme' compared to 'Tifdwarf'.

The following is a detailed description of the characteristics of the new variety as observed at the Mississippi Agriculture and Forestry Experiment Station. The principal distinguishing features noted below are alphabetically itemized for facile contrast with the closest known bermadagrass cultivar, which are also described below.

The New Variety: unclipped 'MS-Supreme' bermudagrass (*Cynodon magenisii*).

a. Leaf color is forest green and rated a 7.5 GY 5/6 using a Munsell© Color Chart for plant tissue. There is no anthocyanin pigmentation expressed in leaves during the fall. however, the leaf pigmentation of 'MS-Supreme' darkens to a 7.5 GY 4/6 using a Munsell© color chart for plant tissue during the fall season and after periods of overcast weather conditions.

b. The grass has a dense canopy of leaves that originates from a prostrate base of creeping, strong stolons. Rhizomes are branched profusely. Stolon color is 5 GY 6/4 using a Munsell© Color Chart for plant tissue. There is no anthocyanin pigmentation expressed in stolons during the fall. The average stolon internode diameter is 0.5 mm, the average stolon node diameter is 1.10 mm, and average stolon internode length is 10.6 mm.

c. The grass has an extensive fibrous root system initiated from the nodes of stolons and rhizomes.

d. Leaves are folded in the bud shoot; the blades are mostly flat with only the midvein slightly visible; and the leaf tip is tapered to a blunt apex.

e. The grass has not been observed to form inflorescence.

f. The grass blade is glabrous on the abaxial and adaxial surface. The ligule consists of a fringe of hairs. The sheath is glabrous, split with margins overlapping, and pubescence tufted at the side of the ligule. The collar is a continuous narrow band, glabrous and auricles are absent.

g. The grass has a somatic chromosome number of 27 and is classed as a triploid.

Provided hereinbelow are the respective characteristics of both i) 'Tifdwarf' (*Cynodon dactylon*×*C. transvaalensis,* the closest known Cynodon cultivar), and ii) 'Tifgreen' (*Cynodon dactylan*×*C. transvaalensis,* the Cynodon cultivar from which 'MS-Supreme' emerged).

Detailed description of unclipped 'Tifdwarf' bermudagrass (*Cynodon dactylon*×*C. transvaalensis*) the closest known Cynodon cultivar.

a. Leaf color is olive green and rated a 7.5 GY 5/4 using a Mundell© Color Chart for plant tissue. There is anthocyanin pigmentation expressed in leaves during the fall, The average leaf width is 1.7 mm and average length 24.9 mm.

b. The grass has a dense canopy of leaves originating from a prostrate base of creeping stolons. Rhizomes are branched profusely. Stolon color is 5 GY 6/4 using a Munsell© Color Chart for plant tissue. There is anthocyanin pigmentation expressed in the stolons during the fall. The average stolon internode diameter is 0.6 mm, the average stolon node diameter is 1.20 mm, and average stolon internode length is 14.3 MM.

c. The grass has an extensive fibrous root system initiated from the nodes of stolons and rhizomes.

d. Leaves are folded in the bud shoot; the blades are mostly flat or slightly V-shaped with only the midvein visible; and the leaf tip is tapered to an blunt apex.

e. The grass has a moderate frequency of inflorescence formation having an average density of 185 inflorescence per square meter. Average height of culms is 18 mm. The inflorescence consists of 2 to 3 digitate spikes at the top of the main stem, folded down at a 30 to 40 deg. angle from vertical, spikelets sessile and closely appressed. The average length of each spike is 28 mm.

f. The grass blade is glabrous on the abaxial and adaxial surface. The ligule consists of a fringe of hairs. The sheath is glabrous, split with margins overlapping, and pubescence tufted at the side of the ligule. The collar is a continuous narrow band, glabrous and auricles are absent.

g. The spikelets are glabrous in two rows, blunt at their base and pointed at their tips. Spikelets are attached an average distance of 1.33 mm along the spikes, borne singly on short branches. The length of an average spikelet is 2.0 mm with glumes extending ⅓ to ½ the length of a floret. The spikelet has stigmas of light purple-red color rates as a 5 RP 7/8 using a Munsell© Color Chart for plant tissue.

h. The grass has a somatic chromosome number of 27 and classed as a triploid.

A detailed description of unclipped 'Tifgreen' bermudagrass (*Cynodon dactylon*×*C. transvaalensis*), the Cynodon cultivar from which 'MS-Supreme' emerged.

a. Leaf color is lime green and rated a 7.5 GY 5/8 using a Munsell© Color Chart for plant tissue. There is no anthocyanin pigmentation expressed in leaves during the fall. The average leaf width is 1.9 mm and average length 39.1 mm.

b. The grass has a dense canopy of leaves erect from a prostrate base of creeping stolons. Rhizomes are branched profusely. Stolon color is 5 GY 6/8 Munsell© Color Chart for plant tissue. There is no anthocyanin pigmentation expressed in stolons during the fall. The average stolon internode diameter is 0.7 mm, the average stolon node diameter is 1.25 mm, and average stolon internode length is 19.9 mm.

c. The grass has an extensive fibrous root system initiated from the nodes of stolons and rhizomes.

d. Leaves are folded in the bud shoot; the blades are mostly flat or slightly V-shaped with only the midvein visible; and the leaf tip is tapered to an acute apex.

e. The grass has a moderate frequency of inflorescence formation having an average density of 235 inflorescence per square meter. Average height of culms is 30 mm. The inflorescence consists of 2 to 3 digitate spikes at the top of the main stem, folded down at a 30 to 40 deg. angle from vertical, spikelets sessile and closely appressed. The average length of each spike is 32 mm.

f. The grass blade is glabrous on the abaxial and adaxial surface. The ligule consists of a fringe of hairs. The sheath is glabrous, split with margins overlapping, and pubescence tufted at the side of the ligule. The collar is a continuous narrow band, glabrous and auricles are absent.

g. The spikelets are glabrous in two rows, blunt at their base and pointed at their tips. Spiklets are attached an average distance of 1.73 mm along the spikes, borne singly on short branches. The length of an average spikelet is 2.3 mm with glumes extending ⅓ to ½ the length of a floret. The spikelet has stigmas of light purple-red color rated as a 5 RP 7/8 using a Munsell© Color Chart for plant tissue.

h. The grass has a somatic chromosome number of 27 and classed as a triploid.

Additional Measurements on MS-Supreme Bermudagrass

Disease Resistance and Susceptibility

Experimental plots located on the Mississippi State University practice green, the Houston Country Club practice green, the Tupelo Country Club practice green, Burning Tree Country Club, the Sturgis Sod Farm Foundation plating, NTEP On-Site Bermudagrass Test locations and Deerfield Country Club in Jackson, Miss. have been evaluated for disease and/or insect infestations. To date, there have been no symptoms of disease or insect infestation at any test location that has allowed for disease resistance and susceptibility ratings. It is assumed that 'MS-Supreme' has similar disease resistance and susceptibility compared to other bermudagrass cultivars used in these tests.

Shoot Density and Thatch Accumulation

Shoot density and thatch accumulation of bermudagrass were measured on a two-year old cultivar evaluation green planted at Colonial-Deerfield Country Club in Jackson, Miss. A two-inch diameter plug was randomly selected from each of three plots of 'Tifdwarf' and 'MS-Supreme'. Thatch accumulation was assessed by measuring from the base of the turf canopy to the soil level of each plug. Without intense cultivation and control, 'MS-Supreme' accumulated significantly more thatch than 'Tifdwarf' (see Table 1). Shoot density was determined by counting the number of live shoots on each plug sample and dividing by the area of the plug. As seen in Table 1, 'MS-Supreme' had significantly higher shoot density than 'Tifdwarf'.

Plant Height

Plant height was determined in a green house study conducted at Mississippi State University in 1999. Three pots each of 'Tifgreen', 'Tifdwarf', and 'MS-Supreme' were allowed to grow for eight weeks without vertical clipping. The average height of the canopy was measured in each of the pots. The plant height of 'MS-Supreme' was significantly shorter than 'Tifgreen' and 'Tifdwarf' (see Table 2).

Sod Strength

Sod strength was determined at Mississippi State University in 1999 from three-year old plots of 'Tifgreen' and 'MS-Supreme' growing adjacently on sandy loam soil. Three 4×1.5-foot strips of sod were randomly cut from each plot area using a commercial sod harvester. Sod strips were harvested to a 0.5-inch soil depth. Each sod strip was broken at three points using a sod stretching device designed to measure the force required to shear the sod. As shown in Table 2, the sod strength of 'MS-Supreme' was significantly greater than the sod strength of 'Tifgreen'.

Low Temperature Kill

A cultivar evaluation trial planted on a putting green at Mississippi State University Golf Course that included 'Tifgreen', 'Tifdwarf', and 'MS-Supreme' was destroyed by low-temperature kill in the abnormally severe winter of 1995–1996. As a result, the entire experiment had to be replanted. In the following three winters (1996–1997; 1997–1998; 1998–1999), there has been no significant winter injury to any of the cultivars at this site.

TABLE 1

Shoot density and thatch accumulation of bermuda grass cultivars measured at Colonial-Deerfield Golf Course in 1999.

| Cultivar | Shoot Density (Shoots/cm$^3$) | Thatch (mm) |
|---|---|---|
| Tifdwarf | 5.7 | 14.8 |
| MS-Supreme | 13.3* | 19.3* |

*Significance at the 0.05 level of probability.

TABLE 2

Plant height and sod strength of bermudagrass cultivars measured at Mississippi State University in 1999.

| Cultivar | Plant Height (cm) | Sod Strength (pounds) |
|---|---|---|
| Tifgreen | 12.7 | 23.1 |
| Tifdwarf | 9.8 | — |
| MS-Supreme | 5.3 | 39.4 |
| LSD (0.05) | 1.0 | 4.1 |

EXPERIMENTATION

Evaluation of the Performance of 'MS-Supreme' on Golf Putting Greens

'MS-Supreme' was submitted to the National Turfgrass Evaluation Program (NTEP) for testing. The NTEP coordinates evaluation of turfgrass varieties across the United States. Test results are used to determine the adaptation of cultivars for nationwide application, localized areas, and levels of turf maintenance. In 1998, the NTEP, in cooperation with the US Golf Association and the Golf Course Superintendents Association, initiated an on-site test to evaluate the performance of bermudagrass cultivars on golf putting greens. 'MS-Supreme' is one of seven cultivars included in this test that was planted at eight golf courses across the nation. Data from these sites was collected by NTEP and summarized in the Progress Report 1998 (NTEP No. 99-4). The performance of 'MS-Supreme' to 'Tifgreen' and 'Tifdwarf' is compared below according to the data that was collected at each site in the establishment year of what is planned to be a four-year experiment.

Location Results

The on-site evaluation of bermudagrass for putting greens was planted at the Country Club of Birmingham, Ala. on Jun. 11, 1998. After establishiment, the test was mowed six times weekly at 0.15 inches height. When rated five weeks after planting, the establishment of 'MS-Supreme' was equal to 'Tifdwarf' and was not significantly lower than 'Tifgreen'. In June and July, the color of 'MS-Supreme' was not signficiantly different from 'Tifgreen' and 'Tifdwarf'. In August, the color of 'MS-Supreme' was significantly darker than 'Tifgreen'. By September, the color of 'Tifgreen' and 'Tifdwarf' had declined and 'MS-Supreme' was significantly darker than both 'Tifgreen' and 'Tifdwarf'. The mean turf quality rating of 'MS-Supreme' (June-September) was significantly higher than 'Tifgreen' and 'Tifdwarf'.

At Mobile, Ala., the test was planted on Jun. 18, 1998 at the Mobile Country Club. After establishment, the green was mowed each day a 5/32 inch height. The establishment of 'MS-Supreme' was not significantly different from 'Tifgreen' or 'Tifdwarf'. The leaf texture of 'MS-Supreme' was rated equal to 'Tifdwarf' and signficantly finer than 'Tifgreen'. The mean turf quality rating of 'MS-Supreme' was significantly higher than either 'Tifgreen' or 'Tifdwarf'.

The on-site test in Green Valley, Ariz., was planted at the Green Valley Country Club, during July, 1998. Because of a lack of irrigation and water supply, this site was planted with turf plugs rather than by the normal sprigging method. The green was not mowed regularly in 1998. Under these conditions, the early establishment of 'MS-Supreme' was rated significantly slower than 'Tifgreen' and 'Tifdwarf'. By fall, differences in percent coverage of 'Tifgreen', 'Tifdwarf', and 'MS-Supreme' were no longer significant. Differences in leaf texture, color, and mean turf quality were not significant.

At the SCGA Members Club in Murietta, Calif., the on-site test was planted on May 23, 1998. The green was mowed five times weekly at ¼ inch height. At five weeks after planting, the establishment of 'MS-Supreme' was rated equal to 'Tifgreen' and significantly faster than 'Tifdwarf'. At ten weeks, the establishment of 'MS-Supreme' was rated between that of 'Tifgreen' and 'Tifdwarf'. 'Tifdwarf' remained slower but not significantly slower than 'MS-Supreme'.

At Hobe Sound, Fla., the test was planted at The Jupiter Island Club. The green was mowed daily at ⅛ inch height. Percent establishment was rated at two-week intervals. On Jul. 14, 1998, establishment of 'MS-Supreme' was significantly higher than 'Tifdwarf' but not significantly higher than 'Tifgreen'. On Aug. 1, 1998, 'Tifgreen' received the highest estabishment estimate, which was significantly higher than 'Tifdwarf', but not significantly higher than 'MS-Supreme'. On Aug. 14, 1998, both 'Tifgreen' and 'MS-Supreme' received significantly higher establishment estimates than 'Tifdwarf'. By Aug. 29, 1998, when establishment was approaching 100 percent, there was no significant difference in these three cultivars. At this location, 'Tifdwarf' was rated with a darker green color and higher turf density than 'MS-Supreme' and 'Tifgreen'. 'MS-Supreme' displayed higher density and finer leaf texture than 'Tifgreen'. Mean turf quality ratings of 'MS-Supreme' and 'Tifdwarf' were significantly higher than 'Tifgreen'.

The Missouri Bluffs Golf Course site at St. Charles, Mo. was planted on Jun. 10, 1998. The green was mowed three times weekly at 3/16 inch height. An establishment estimate made in summer found no significant differences in 'MS-Supreme', 'Tifdwarf', and 'Tifgreen'. A fall estimate found that 'MS-Supreme' and 'Tifgreen' had established significantly faster than 'Tifdwarf'. There were no significant differences in mean turb quality among the three cultivars. 'MS-Supreme' and 'Tifdwarf' were rated with significantly finer leaf texture than 'Tifgreen'. The color of 'Tifdwarf' was rated darker than 'MS-Supreme' and 'Tifgreen' at this site.

At Dallas, Tex., the test was planted at The Bent Tree Country Club on Jun. 8, 1998. The green was mowed six times weekly at ⅛ inch height. Af five weeks after planting, the estimated percent establishment of 'MS-Supreme' was between that of 'Tifgreen' and 'Tifdwarf'. At eight weeks, the establishment of 'MS-Supreme' was equal to 'Tifgreen' and significantly higher than 'Tifdwarf'. Differences in genetic color among these three cultivars was not significant. A winter color rating found 'MS-Supreme' to be significantly darker green than 'Tifdwarf' and 'Tifgreen'.

At Houston, Tex., the on-site test was planted at the Lakeside Country Club on Jun. 16, 1998. This green was mowed daily at 5/32 inch height. Establishment of 'MS-Supreme' was equal to 'Tifgreen' and not significantly greater than 'Tifdwarf'. The mean turf quality ratings of 'MS-Supreme' and 'Tifdwarf' were significantly higher than 'Tifgreen'. The genetic color rating of 'MS-Supreme' was equal to 'Tifdwarf' and significantly darker than 'Tifgreen'.

Conclusion

'MS-Supreme' performed well in the establishment year of a nationwide test in the application for which it is recommended. At four out of the eight locations, 'MS-Supreme' established significantly faster than 'Tifdwarf'. Only at Green Valley, Ariz., where the green was not mowed regularly, did 'Tifdwarf' establish significantly faster than 'MS-Supreme'. At five out of seven locations where turf quality was rated in 1998, 'MS-Supreme' received significantly higher ratings than 'Tifgreen'. At two locations, the turf quality of 'MS-Supreme' was significantly higher than 'Tifdwarf'. At two out of six locations where color was rated, 'MS-Supreme' maintained a darker green color than 'Tifgreen'. In Birmingham, Ala. and Dallas, Tex., the late-season color of 'MS-Supreme' was significantly darker green than 'Tifdwarf'. At all four locations where leaf texture was rated, 'MS-Supreme' was significantly finer than 'Tifgreen'. The first-year results of the NTEP on-site test further confirm than 'MS-supreme' is genetically and morphologically different from 'Tifgreen' and 'Tifdwarf' and performs differently from 'Tifgreen' and 'Tifdwarf' under golf green culture.

As will be apparent to those skilled in horticultural science, the new variety as herein described may vary in slight detail due to climate, soil and cultural conditions under which the variety may be grown, and the stage of growth.

What is claimed and desired to be secured by Letters Patent of the United States is:

1. A new and distinct variety of bermudagrass plant, substantially as herein described and illustrated.

* * * * *